United States Patent [19]
Ichiki et al.

[11] Patent Number: 5,591,886
[45] Date of Patent: Jan. 7, 1997

[54] PROCESS FOR THE CRYSTALLIZING L-α-ASPARTYL-L-PHENYLALANINE METHYL ESTER FROM THE SOLUTION

[75] Inventors: Hiroshi Ichiki; Ryoichi Taneda; Hiroyuki Itoh; Yoshitsugu Kono, all of Ohmuta, Japan

[73] Assignee: Mitsui Toatsu Chemicals, Incorporated, Tokyo, Japan

[21] Appl. No.: 445,346

[22] Filed: Jun. 16, 1995

Related U.S. Application Data

[63] Continuation of Ser. No. 175,044, Dec. 29, 1993, abandoned, which is a continuation-in-part of Ser. No. 788,268, Nov. 5, 1991, abandoned.

[30] Foreign Application Priority Data

Nov. 5, 1990 [JP] Japan .................................. 2-297119

[51] Int. Cl.$^6$ .................................................. C07C 229/00
[52] U.S. Cl. .............................. 560/41; 23/295 R; 560/40
[58] Field of Search ........................... 23/295 R; 422/252, 422/245; 560/40, 41

[56] References Cited

U.S. PATENT DOCUMENTS

| | | | |
|---|---|---|---|
| 1,997,277 | 4/1935 | Burke et al. | 422/245 |
| 2,288,667 | 7/1942 | Allen et al. | 422/245 |
| 2,337,317 | 12/1943 | Eggert | 62/123 |
| 3,829,293 | 8/1974 | Waquier et al. | 422/245 |
| 4,897,506 | 1/1990 | Mita et al. | 560/41 |
| 5,041,607 | 8/1991 | Naruse et al. | 560/41 |

FOREIGN PATENT DOCUMENTS

| | | | |
|---|---|---|---|
| 128694 | 12/1984 | European Pat. Off. | |
| 255092 | 2/1988 | European Pat. Off. | 560/41 |
| 484769 | 5/1992 | European Pat. Off. | 560/41 |
| 73-22893 | 7/1973 | Japan | 422/252 |
| 1-37173 | 8/1989 | Japan . | |
| 1489028 | 10/1977 | United Kingdom . | |

OTHER PUBLICATIONS

Perry, J. H., ed. "Chemical Engineers' Handbook", McGraw Hill: New York (1950), pp. 1061–1069.
Kirk–Othmer, "Encyclopedia of Chemical Technology" 3rd Ed., vol. 7. (1980), pp. 263–265; 268–273.
Considine, D. M., ed. "Chemical and Process Technology Encyclopedia", McGraw–Hill:New York (1974) p. 742.
Chem. Abstracts 111:95773b. (1989).

*Primary Examiner*—Michael Lewis
*Assistant Examiner*—Peter T. DiMauro
*Attorney, Agent, or Firm*—Millen, White, Zelano, & Branigan, P.C.

[57] ABSTRACT

Disclosed herein is a crystallization apparatus for use in the crystallization of L-α-aspartyl-L-phenylalanine methyl ester. The stirring blade of the crystallization apparatus is composed of a band plate member for sweeping the bottom of a vessel and rod- or band plate-members arranged thereon and extending substantially vertically and horizontally.

9 Claims, 3 Drawing Sheets

1

PROCESS FOR THE CRYSTALLIZING L-α-ASPARTYL-L-PHENYLALANINE METHYL ESTER FROM THE SOLUTION

This application is a continuation of application Ser. No. 08/175,044, filed Dec. 29, 1993 now abandoned, which is a continuation-in-part of application Ser. No. 07/788,268 filed Nov. 5, 1991, now abandoned.

BACKGROUND OF THE INVENTION

1. Field of the Invention

This invention relates to a crystallization process of L-α-aspartyl-L-phenylalanine methyl ester which is easy to handle in the filtration and dehydration operations.

2. Description of the Related Art

L-α-aspartyl-L-phenylalanine methyl ester (hereinafter referred to as to APM) is a substance expected to be used widely as a low-caloric sweetening agent owing to its excellent sweetness. A variety of processes have so far been known to produce APM industrially. Upon execution of any of these processes, however, a crystallization step is indispensable in order to isolate APM from the reaction solution to prepare it as a product.

Generally in the crystallization step, a crude product is dissolved again in water, an organic solvent or a hydrated organic solvent, and the resultant solution is allowed to cool through heat-exchange with a coolant or partial vaporization of the solvent under reduced pressure to deposit the crystals in a crystallization apparatus equipped with stirring blades, the crystals being then filtered or dehydrated by means of a centrifuge or the like. There is also known a process for preparing the crystals which comprises cooling an aqueous APM solution of a certain concentration or higher through conduction heat transfer without giving forced movement such as mechanical agitation to obtain an apparent ice-cream-like pseudo-solid and, if necessary, cooling further the pseudo-solid thus formed.

However, in the case of using crystallization apparatuses equipped with conventional stirrers, APM obtained, for instance, in a crystallization apparatus with a paddle- or turbine-type stirring means presents a fine needle-like crystal habit so that its solid-liquid separation in filtration or dehydration is very insufficient, thus raising serious problems upon practice.

Further, when the solid-liquid separation is repeated, the basal layer of the cake becomes hard by compression and its removal takes many hours to complete. Moreover, in a drying step subsequent to the crystallization step, the larger moisture content of the cake leads to a higher drying load, and the larger bulk specific volume of the resulting dry powder also causes its handling to be very difficult.

A process, in which cooling is effected only by conduction heat transfer without agitation of the system, takes a very long time to operate and hence can hardly be put into industrial practice.

SUMMARY OF THE INVENTION

The present invention provides a process wherein crystallization of APM from its solution is effected using a crystallization apparatus of a specific structure.

The crystallization apparatus is composed of a vessel, a stirrer comprising a revolving shaft and stirring blades, each blade comprising a band plate member capable of sweeping the bottom of the vessel and rod- and band plate-members provided thereon which extend horizontally and vertically, and baffle plates.

Figure 1:
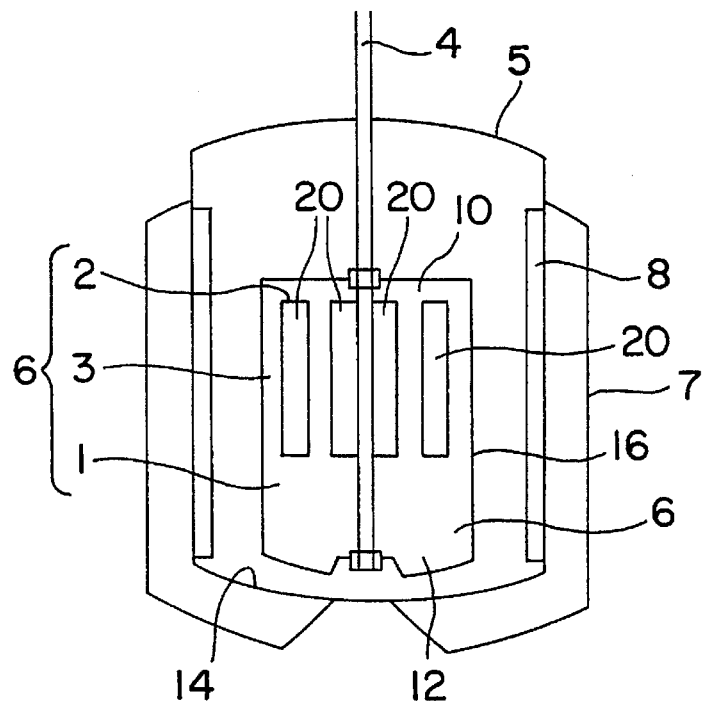
FIGS. 1 through 5 show crystallization apparatus having a vessel and a stirrer with stirring blades useful in the practice of the present invention.

Numerals 1, 2, 3 and 4 stand for a first member, a second member, a third member; a revolving shaft, further, numeral 5 stands for vessel, 6 for a stirring blade, 7 for a jacket and 8 for a baffle, respectively.

DETAILED DESCRIPTION OF THE INVENTION

In the present invention, APM is crystallized out under agitation of an APM solution by means of a specific crystallization apparatus as defined in herein.

The inner walls of the crystallizer are provided with a plural number of baffle plates vertically from the bottom to the top along the axial direction. APM solutions that can be treated may have a wide range of concentrations. For example, the concentration of APM in aqueous state may range from 2% by weight to the aqueous saturated solution. The concentrations of from 3.5 to 4% by weight may preferably be mentioned.

The crystallization temperature may range from 80° C. to 0° C., preferably from 60° C. to 5° C. In the crystallization of APM, the solution is allowed to cool slowly while maintaining the peripheral speed of the aforementioned stirring blade at 0.1–1.2 m/sec, preferably at 0.3–0.6 m/sec.

Cooling of the crystallizing solution is effected by circulating a coolant through a jacket arranged on the outside of the vessel, by means of vacuum evaporation, or by a combination of these means.

The stirring blade used in the present invention will be described as follows. Stirring blades are fixed to a revolving shaft installed in the center of the vessel at one end of each blade. As a matter of course, the stirrer may comprise an odd number, except one, of stirring blades, provided that a smooth rotation of the shaft is ensured. However, it is recommended that the stirrer have two stirring blades arranged symmetrically in view of the easiness of fabrication.

A first member constituting the blade is substantially a band plate, sweeping the bottom of the vessel. The space between the lower end of the plate and the bottom of the vessel is preferably as small as possible. Although the reason is not clear, it appears preferable that the liquid flow toward the bottom of the vessel is not large.

It is desirable that there is a certain degree of space between the end of each stirring blade facing the inner walls of the vessel and the inner walls. This is for the purpose of forming liquid flows toward the inner walls.

A second member is practically a rod member provided above the first member and extends from the revolving shaft to the inner walls of the vessel. In other words, it is an arm extending from the revolving shaft. The number of this member is not necessarily limited to one; therefore, a plurality of the members may be disposed in horizontally parallel in a vertical plane. The limitation of the length is the same as that of the first member and can be made shorter. The direction in which the rod member extends may not particularly be parallel to the liquid surface but may be aslant so far as the member is so disposed as to cut across the liquid substantially horizontally.

A third member is a rod- or band plate-member extending substantially vertically in the liquid and agitates the liquid. It may be fixed to only either one or to both of the first and second members, so far as its mechanical strength for agitating the liquid is maintained. No strict limitation is imposed on the direction of the member, and it is sufficient if the member is directed practically vertically. Further, it is enough if the member is installed by way of the first and/or second member so that it can move to cut across the liquid flowing from the inner walls of the vessel to the revolving shaft. A plural number of the members is permitted in a unit stirring blade.

The most common arrangement of the foregoing three members is such that they are disposed in the same vertical plane to form, as a whole, a lattice plate with spaces (voids) in it. However, it is also quite allowable that the plate as a whole constitutes a twistedly curved surface.

Figure 6:
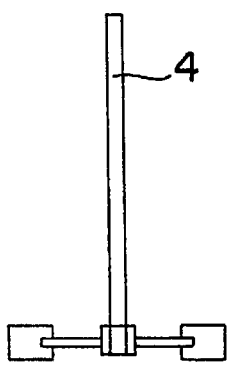
FIGS. 6 through 8 illustrate various stirring blades which are not used in the present invention.
Figure 7:
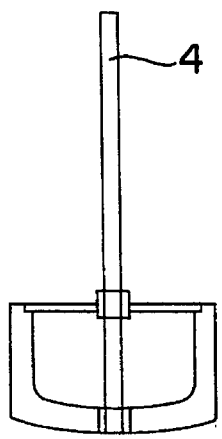
Figure 8:
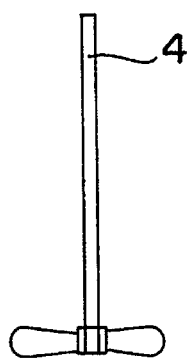

The configurations of the stirring blades of the present invention are as illustrated in FIGS. 1 to 5. Those shown in FIGS. 6 to 8 are not to be used in the present invention.

Considering in greater detail the structure of the vessel 5, exterior extending baffles 8, cooling jacket 7 and stirring blades 1, it is seen that the stirring blades 1 mounted on hollow rods 4 serve the dual purpose of both rotating the stirring blades and applying a vacuum to the vessel 1 by drawing a vacuum therethrough. Each stirring blade has a top portion 10 and a bottom portion 12, the bottom portion 12 sweeping the bottom 14 of the container 1 as the blade is rotated. Each blade 1 has a side edge 16 which inherently shears the solution contained within the vessel 1. As the blades 1 rotate in the solution, the solution passes through openings 20 in the embodiment of FIG. 1, 22 in the embodiment of FIG. 2, 24 in the embodiment of FIG. 3, 26 in the embodiment of FIG. 4, and 28, 30, and 32 in the embodiment of FIG. 5.

As is seen in FIG. 1, the openings 20 in the stirring blade 1 are comprised of vertically extending slots which are spaced from the tops 10 and bottoms 12 of the blades. As is seen in FIG. 2, the openings 22 in each stirring blade 1 are arranged in pairs of vertically extending slots vertically spaced from one another and from the side edges 16 of the stirring blades.

Figure 3:
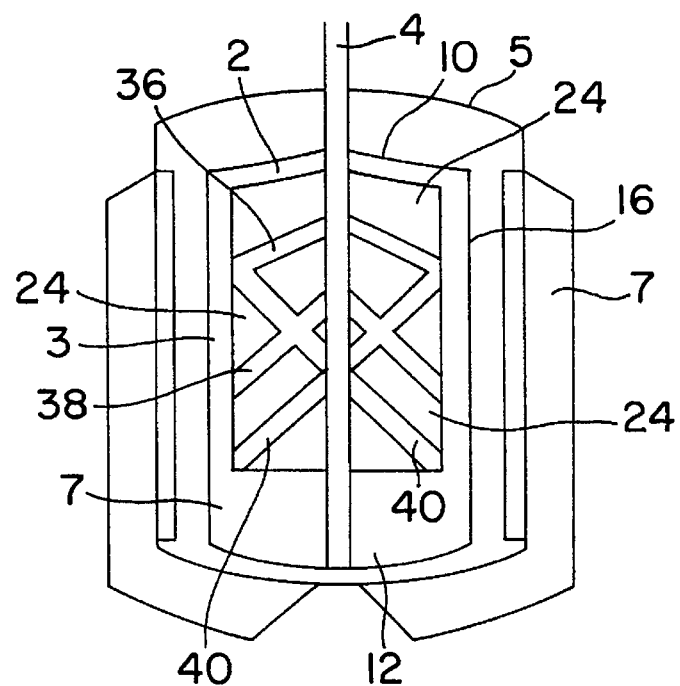
Figure 4:
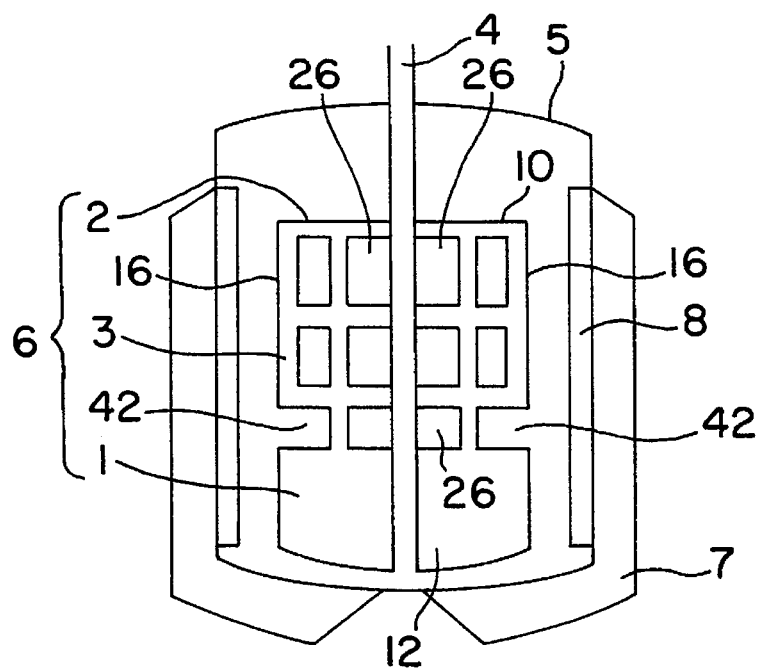

As is seen in FIG. 3, the openings 24 are defined by an array of struts 36, 38, and 40.

Figure 2:
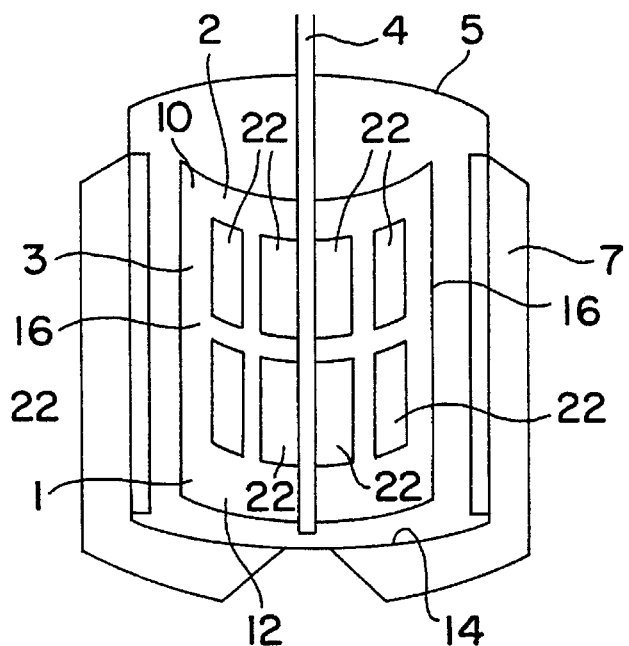

In the embodiment of FIG. 6, the openings 26 are similar to the openings of FIG. 2. However, there are lateral openings 42 which are not spaced from the side edges 16 of the stirring blades.

Figure 5:
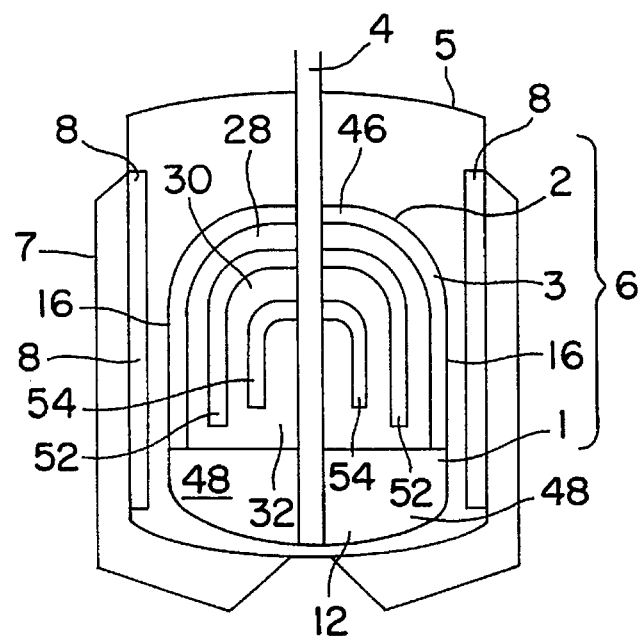

Referring now to FIG. 5, it is seen that the openings 28, 30, and 32 in each blade 1 are defined by a first L-shaped strut, which extends laterally from the hollow rod 4 and axially to the panel 48, forming the bottom 12 of the stirring blade, the axially extending portion of the strut extending substantially parallel to the baffles 8. Disposed within the first L-shaped strut are second and third L-shaped struts 52 and 54, which extend substantially parallel to the first L-shaped strut but do not contact the bottom panel 48.

According to the process of the present invention, it is possible to obtain crystals with good filtration characteristic under the agitation of a crystallizing solution. In other words, crystals of APM are deposited continuously while maintaining the liquid flowability satisfactorily, and the crystals thus obtained exhibit good handling properties in the subsequent steps of transportation, separation, drying, etc. and also are very resistant to physical impact.

Generally, the crystals deposited stick to the heat transfer surface to form so-called "scaling", often causing great difficulty in the removal thereof. However, in the crystallization of APM according to the process of the present invention, it is very easy to remove or take off the crystalline layer from the cooling surface.

Since APM crystals with good filtration characteristics can be obtained according to the present invention, remarkable improvements can be achieved not only in the solid-liquid separability of the product, but also in the miniaturization of the apparatus because of the reduction in crystallization time, load on the dryer and operations for each step. Further, even when the process of the present invention is applied to an APM solution containing impurities such as diketopiperazine (DKP), that is a cyclization product of APM, and L-α-aspartyl-L-phenylalanine, it is possible to obtain APM crystals without these impurities because of the reduction in the amount of remaining mother liquor and the improvement in cake washability in the solid-liquid separation step. Thus, the present invention provides an APM crystallization process that is markedly advantageous from economic viewpoint.

With stirrers of conventional stirring blades as shown in FIGS. 6 to 8, as the agitation speed is increased, crystals of APM become smaller. On the contrary, when the speed is decreased, the flowability is worsened, causing the crystals to stick to the crystallizer causing problems.

The present invention will be described more specifically with reference to the following examples.

EXAMPLE 1

This example was performed by installing a stirrer with stirring blades of FIG. 1 in a crystallizer. A crystallizer 1 is a vertically-cylindrical jacketed vessel with a capacity of 300 liters, which has an inner diameter of 700 mm and a height of 850 mm and is provided with four baffle plates in the interior thereof.

The stirring blades used has a D of 420 mm and an H of 760 mm.

In the crystallizer was charged 250 liters of a starting solution in which 9.5 kg of APM containing 3% of DKP had been dissolved (60° C.; the initial concentration of APM was 3.6% by weight). Then, the revolution of the stirring blades was adjusted at 30 rpm, with a peripheral speed of the stirring blades of about 0.66 m/sec (calculated from the 420 mm diameter stirring blade sweeping around the vertically-cylindrical vessel at 30 rpm), and a coolant of 10° C. was circulated through a jacket 7. Thus, crystallization was carried out by cooling the solution always from the interior thereof, that is, by controlling the temperature and vacuum inside the crystallizer under reduced pressure by a vacuum pump 4. After about 40 minutes from starting the experiment, crystals began to deposit in the solution. The temperature of the solution at this time was 40° C. After a lapse of one hour, the solution was entirely filled with the crystals. Then, the solution was cooled to 7° C. by circulating the coolant of 0° C. The crystallization was completed after three hours from the initiation of the experiment.

The slurry thus obtained was filtered and dehydrated by means of a centrifuge, with the result that the moisture content of the cake was reduced to 40% after 20 minutes. The yield was 12.5 kg (wet basis), the rate of recovery was 80%, and the content of DKP was 0.1%.

Comparative Example 1

This comparative example was performed by installing a stirrer with blades of FIG. 6 i.e., blades of flat blade turbine type with D=400 mm. Crystallization was carried out in the same manner as in Example 1, except that the revolution was set at 100 rpm in view of the characteristics of the stirring blades. In the course of crystallization, a portion wherein the slurry did not flow was evolved, and a lot of stickings to the inner walls were found upon discharge. The moisture content was 60% or more even after more than two hours of the subsequent filtration and dehydration. The rate of recovery was 60% because of filtration leakage.

EXAMPLE 2

Using the same stirring blades (D: 420 mm, H: 760 mm) and APM solution as those used in Example 1, crystallization was carried out under atmospheric pressure by regulating the revolution of the stirring blades at 50 rpm with a peripheral speed of the stirring blades of about 1.1 m/sec (calculated from the 420 mm diameter stirring blade sweeping around the vertically-cylindrical vessel at 50 rpm), and circulating a coolant through the jacket. The temperature of the coolant was 10° C. until the crystals began to deposit, and thereafter the coolant of 0° C. was circulated. The crystallization was completed when the solution was cooled to 7° C. The whole time of crystallization was about 4 hours.

The slurry thus obtained was filtered and dehydrated by means of a centrifuge, with the result that the moisture content of the cake after 20 minutes was 40%, the yield was 12.5 kg (wet basis), and the rate of recovery was 80%.

Although operations were carried out batchwise in all of the above-described examples, continuous operation is also possible industrially.

As is clear from the foregoing description and examples, the present invention has merits in the following respects in the steps of crystallizing and separating APM.

(1) It is possible to employ a conventional vertically-cylindrical vessel, without need for particular equipment except for the stirring blades.

(2) With the slurry containing APM crystals obtained according to the process of the present invention, solid-liquid separation can be effected in a shorter time than with those derived from conventional processes.

(3) Since the separability of crystals is remarkably improved, higher washing effects are achieved and hence products with little impurities can be obtained.

(4) The load in the drying step can be reduced, and good handling properties of the dry powder can be expected.

We claim:

1. A process for crystallizing L-α-aspartyl-L-phenylalanine methyl ester, APM, specifically to form crystals thereof from a solution thereof, the method comprising the steps of:

containing the solution in a vessel having a bottom and a sidewall, the sidewall having vertically extending baffles extending inwardly thereof;

while cooling the solution to a first temperature by cooling the vessel, minimizing deposition of crystals on the bottom and sidewalls of the vessel by stirring the solution with a stirrer on a rod rotating about a vertical axis in a range of about 30 to about 50 RPM to form crystals of APM and to keep the crystals suspended in the solution, the stirrer having vertically extending stirring blades located in closer proximity to the bottom of the vessel than to the baffles to sweep the bottom of the container, with a peripheral speed of the stirring blades of about 0.66 to about 1.1 m/sec, the stirring blades each having a plurality of openings therethrough and vertical side edges and bottom edges, the openings being spaced from the bottom edges of the blades, wherein the solution is agitated by passing through the openings in the blades as well as by passing between the stationary baffles and the vertical side edges of the blades to create a slurry of liquid and crystals;

while stirring and cooling the solution, maintaining a reduced pressure within the vessel by applying a vacuum thereto as the blades are rotated;

upon the solution substantially filling with crystals, cooling the solution as to form a slurry of liquid and crystals;

filtering the slurry to separate the crystals from the fluid; and dehydrating the crystals.

2. A process for providing crystallized, L-α-aspartyl-L-phenylalanine methyl ester, APM, to separate the APM from a reaction solution in which the APM was formed, the method comprising the steps of:

containing the reaction solution which is initially at a temperature of about 60° C. in a vessel having a bottom and a sidewall, the sidewall having vertically extending baffles extending inwardly with respect thereto;

cooling the reaction solution from the initial temperature of about 60° C. to a crystallization temperature of about 40° C. to form an initial slurry of liquid and AMP crystals;

while cooling the reaction solution, stirring the reaction solution by rotating about a vertical axis a stirrer on a rod at a speed in the range of about 30 to about 50 RPM having vertically extending stirring blades, each of which has a plurality of openings therethrough, vertical side edges and bottom edges, with a peripheral speed of the stirring blades of about 0.66 to about 1.1 m/sec, the bottom edges being always closer to the bottom of the vessel than the side edges come to the baffles when the stirrer is rotating, wherein the solution is agitated during stirring and cooling by passing through the openings in the blades as well as by passing between the stationary baffles and the vertical side edges of the blades when making the initial slurry of liquid and APM crystals;

cooling the solution from about 40° C. to about 7° C. to form a final slurry of liquid and APM crystals;

filtering the final slurry to separate APM crystals from the liquid; and dehydrating the APM crystals to form a crystalline cake.

3. The process of claim 2, wherein the vessel has a cooling jacket therearound and wherein the liquid is cooled by circulating cooling fluid through the jacket.

4. The process of claim 2, wherein the openings in the stirring blades are comprised of vertically extending slots spaced from the tops and bottom edges of the blades.

5. The method of claim 2, wherein the openings in each stirring blade are pairs of vertically extending slots, vertically spaced from one another and from the sides, tops, and bottom edges of the blades.

6. The method of claim 2, wherein the openings in each of the blades are formed by at least a first L-shaped strut, a first leg of which extends laterally from the rod and axially to a panel proximate the bottom edges of the stirring blades, the strut having a second leg extending substantially parallel to and spaced from the baffles.

7. The method of claim 6, further including at least one smaller L-shaped strut disposed within a space defined by the first L-shaped strut.

8. The process of claim 2, wherein the concentration of AMP in the solution is in the range of 3.5 to 4.0% by weight.

9. The process of claim 2 further including the step of maintaining a reduced pressure within the vessel by applying a vacuum to the vessel while cooling and stirring the solution.

* * * * *